(12) United States Patent
Slater (10) Patent No.: US 11,896,413 B2
(45) Date of Patent: Feb. 13, 2024

(54) SENSOR SYSTEM FOR AN ACTUATOR, ACTUATOR AND METHOD FOR MOVING AN ACTUATOR PART

(71) Applicant: Ewellix AB, Goeteborg (SE)

(72) Inventor: Conor Slater, Liestal (CH)

(73) Assignee: Ewellix AB, Goeteborg (SE)

(*) Notice: Subject to any disclaimer, the term of this patent is extended or adjusted under 35 U.S.C. 154(b) by 368 days.

(21) Appl. No.: 17/189,540

(22) Filed: Mar. 2, 2021

(65) Prior Publication Data

US 2021/0275119 A1    Sep. 9, 2021

(30) Foreign Application Priority Data

Mar. 4, 2020  (DE) .......................... 102020105759.8

(51) Int. Cl.
| | |
|---|---|
| *A61B 6/00* | (2006.01) |
| *G05D 3/12* | (2006.01) |
| *F16M 11/28* | (2006.01) |
| *G01L 5/00* | (2006.01) |
| *F16M 11/42* | (2006.01) |

(52) U.S. Cl.
CPC ........... *A61B 6/4482* (2013.01); *F16M 11/28* (2013.01); *G01L 5/0061* (2013.01); *G05D 3/12* (2013.01); *F16M 11/42* (2013.01)

(58) Field of Classification Search
CPC ... A61B 6/4482; A61B 6/4476; A61B 6/4429; A61B 6/4405; A61B 6/4411; F16M 11/28; F16M 11/42; F16M 11/18; G01L 5/0061; G01L 5/04; G05D 3/12; G05B 2219/25428; G01P 15/003; B66F 3/44; G01C 21/16

See application file for complete search history.

(56) References Cited

U.S. PATENT DOCUMENTS

| | | | |
|---|---|---|---|
| 4,912,727 A | 3/1990 | Schubert | |
| 9,669,548 B2* | 6/2017 | Tanabe | ................ B25J 19/0075 |
| 10,578,983 B2* | 3/2020 | Butler | ................ G03F 7/70775 |
| 10,731,737 B2 | 8/2020 | Dietrich et al. | |
| 10,814,484 B2 | 10/2020 | Preisinger et al. | |
| 2001/0022831 A1 | 9/2001 | Meek et al. | |
| 2004/0122536 A1 | 6/2004 | Saitou | |
| 2011/0037346 A1 | 2/2011 | Haussecker et al. | |
| 2012/0303193 A1* | 11/2012 | Gresser | ................. B60K 16/00 |
| | | | 903/907 |
| 2014/0022717 A1* | 1/2014 | Bolik | .................... G01L 19/148 |
| | | | 361/679.01 |

(Continued)

FOREIGN PATENT DOCUMENTS

| | | |
|---|---|---|
| CN | 101681982 A | 3/2010 |
| CN | 104810307 A | 7/2015 |

(Continued)

*Primary Examiner* — Mohammad K Islam
(74) *Attorney, Agent, or Firm* — Laurence A. Greenberg; Werner H. Stemer; Ralph E. Locher (57) ABSTRACT

In a sensor system for an actuator, in particular a lifting column, a force sensor is configured to detect a total force acting on an actuator part. An acceleration sensor is configured to detect an acceleration of the actuator part. Accordingly, the sensor system has a processing device, which is configured to control a drive of the actuator for moving the actuator part on a basis of the detected total force and the detected acceleration.

15 Claims, 4 Drawing Sheets

(56) References Cited

U.S. PATENT DOCUMENTS

2014/0148078 A1* 5/2014 Lau .................. A63H 3/28
                                                446/175
2018/0049822 A1   2/2018 Henderson et al.
2020/0016758 A1   1/2020 Keller et al.

FOREIGN PATENT DOCUMENTS

| CN | 107850463 A    | 3/2018  |
|----|----------------|---------|
| CN | 108369406 A    | 8/2018  |
| CN | 108627153 A    | 10/2018 |
| CN | 109571475 A    | 4/2019  |
| CN | 110325329 A    | 10/2019 |
| DE | 3836473 A1     | 5/1990  |
| DE | 102011084295 A1 | 4/2013  |
| DE | 102013217933 A1 | 3/2015  |
| EP | 2857608 A1     | 4/2015  |
| JP | S62205914 A    | 9/1987  |

* cited by examiner

SENSOR SYSTEM FOR AN ACTUATOR, ACTUATOR AND METHOD FOR MOVING AN ACTUATOR PART

BACKGROUND OF THE INVENTION

Field of the Invention

The present invention relates to a sensor system for an actuator, in particular a lifting column, to an actuator having such a sensor system, to a mobile X-ray system having such an actuator, and to a method for moving an actuator part of an actuator, which is mounted movably relative to an actuator base.

The moving of heavy loads usually requires considerable force to be applied by the user. To make such movements easier, it is known to use actuators which assist the movement with the aid of counterweights or spring systems. Although such solutions reduce the effective weight of the load as experienced by the user, they do not reduce the inertia associated with the substantial mass of the load. To execute rapid movements or to accelerate the load, it is therefore still necessary to apply considerable force.

This disadvantage can be overcome by motor-driven actuators. A user can then comfortably move the load by suitable control of the motor, for example by actuation of corresponding buttons or a joystick. However, a disadvantage of this is that the precision of a motor-controlled actuator movement is limited by the speed at which this movement is intended to be carried out.

BRIEF SUMMARY OF THE INVENTION

It is an object of the present invention to further improve the actuator assistance during the movement of a load, in particular to permit a high degree of precision in the positioning of the load, even at a high speed of movement.

This object is achieved by a sensor system for an actuator, in particular a lifting column, by an actuator having such a sensor system, by a mobile X-ray system having such an actuator, and by a method for moving an actuator part of an actuator, which is mounted movably relative to an actuator base, in accordance with the independent claims.

A sensor system for an actuator, in particular a lifting column, according to a first aspect of the invention, has a force sensor and an acceleration sensor. The force sensor is designed to detect a total force acting on an actuator part that is mounted movably relative to an actuator base. The acceleration sensor is designed to detect an acceleration of the actuator part. According to the invention, the sensor system moreover has a processing device, which is designed to control a drive of the actuator for moving the actuator part on the basis of the detected total force and of the detected acceleration.

An actuator part within the meaning of the invention is in particular an actuator component which is movable or is mounted movably with respect to the actuator base, i.e. another actuator component, in particular relative to the actuator base. An example of such an actuator part is a ram or piston which is movable in translation, for example by a motor, with respect to an actuator base designed as a housing, in particular a cylinder. Another example is a for example carriage-like segment of a lifting column which is movable, for example by actuation of a cable pull, relative to a column-like segment of the lifting column as actuator base.

The actuator part is preferably designed to carry a load, e.g. an X-ray head of an X-ray system.

A total force within the meaning of the invention is in particular the sum of all the forces acting on the actuator part, in particular during a movement of the actuator part relative to the actuator base. In the case of a movement of the actuator part guided by a user, the total force can be composed for example of a force exerted on the actuator part for guiding by the user, the (inertial) force associated with the resulting acceleration, and the weight force of the actuator part and/or of a load connected thereto. The total force can be variable over time, particularly in the case of a movement of the actuator part.

One aspect of the invention is based on the approach whereby the force effected by an acceleration on a part of an actuator movable with respect to a base is brought into relation with a measured total force that acts on the actuator part. On the basis of the measured acceleration and of the measured total force, a drive, e.g. a motor, of the actuator can then be controlled for the movement of the actuator part.

From the acceleration or the associated (inertial) force and from the total force, it is possible to preferably obtain a force actively exerted on the actuator part, e.g. by a user in a guided movement of the movable part, or at least a measure of this force. The drive can therefore be controlled, on the basis of the acceleration and of the total force, in such a way that the movement of the actuator part guided by the user is assisted. This allows the user to precisely and quickly position loads, even heavy ones, that are connected to the actuator part. The user is permitted in particular an intuitive movement of such heavy loads. In particular, it is not necessary for the user to operate a special control device, e.g. in the form of a handle or grip, in order to bring about a movement of the actuator part or in order to assist a movement of the actuator part guided by said user. The invention thus allows assistance in the movement of loads without the use of a control device.

In order to detect the acceleration of the actuator part, an acceleration sensor is preferably provided, e.g. in the form of a microsystem (MEMS) on an integrated circuit (IC), and, in order to detect the total force acting on the actuator part, a force sensor is preferably provided, e.g. in the form of a weighing cell. With the aid of a processing device, which may be realized for example as a printed circuit board (PCB) populated with corresponding data acquisition and processing electronics or as an application-specific integrated circuit (ASIC), it is possible for example to determine a measure of the force exerted on the actuator part and to generate corresponding commands for controlling the drive.

For example, the processing device can be designed to precisely determine the force exerted on an X-ray head by a user for the guided movement of the X-ray head, in particular of an X-ray collimator, which is carried by a lifting column and is mounted movably with respect to a movable substructure, e.g. a trolley, with the aid of the lifting column, and to use this force as a basis for controlling a motorized drive of the lifting column. The user can thus accelerate the X-ray head at great speeds with his hands, without applying any great force, and yet can still precisely position it. No special grips or contact points need to be provided for this purpose. Instead, the user can exert force for movement at any point of the X-ray head, which force can be recorded by the force sensor and taken into account for controlling the drive.

Preferred embodiments of the invention and developments thereof are described below, said embodiments each being able to be combined arbitrarily with one another and with the further described aspects of the invention, unless this is expressly ruled out or technically impossible.

In a preferred embodiment, the processing device is designed to use the detected total force and the detected acceleration to determine a measure of a force exerted on the actuator part, in particular by a user for moving the actuator part, preferably by a hand movement of the user, and to control the drive on the basis of said measure. The processing device can in particular be designed to cause the actuator part to track a hand movement of the user on the basis of the determined measure with the aid of the drive, i.e. to cause the drive to have the actuator part track the hand movement. This permits reliable load relief for the user in the movement of the actuator part or of a load connected thereto.

In a further preferred embodiment, the processing device is designed to control the drive on the basis of a stored calibration value. For this purpose, the sensor system, in particular the processing device, can have a memory in which the calibration value is or can be stored. The use of a stored calibration value allows the drive to be controlled in accordance with a forced exerted on the actuator part by a user, without knowing the mass of the actuator part or of the load connected thereto.

In a further preferred embodiment, the stored calibration value corresponds to a total force acting on the actuator part when the actuator part is at rest, i.e. when the actuator part is stationary. The calibration value can correspond in particular to the weight force of the actuator part and/or of a load connected thereto. In this way, the influence of the weight force of the actuator part on the total force detected upon movement of the actuator part can be determined and taken into account in controlling the drive.

In a further preferred embodiment, the force sensor is designed to detect the total force acting on the actuator part, when the actuator part is at rest, in a calibration mode. For this purpose, the sensor system can preferably operate in a calibration mode or can be placed in the calibration mode. The processing device is preferably designed to store as calibration value the total force detected when the actuator part is at rest. This permits precise detection of the weight force of the actuator part or of the load connected thereto.

The sensor system or the actuator is preferably designed to signal the calibration mode to the user. For example, the processing device can be designed to output or enable the output of a corresponding optical or acoustic signal in the calibration mode. It is thus possible to ensure that the user does not exert a force on the actuator part during the detection of the calibration value.

Alternatively or additionally, it is also conceivable that the sensor system or the actuator is designed to block the movement of the actuator part relative to the actuator base in the calibration mode. For example, the processing device can be designed to block the actuator part in the calibration mode with the aid of a locking mechanism, which is provided to simplify the positioning of the actuator part relative to the actuator base. In this way, an accidental movement of the actuator part by the user during the calibration can be prevented.

In a further preferred embodiment, the processing device is designed to normalize the total force, detected by the force sensor, with a total force acting on the actuator part when the actuator part is at rest, i.e. when the actuator part is stationary. The processing device is preferably designed here to normalize the detected total force with the aid of the stored calibration value. In this way, the total force acting on the stationary actuator part can be obtained quickly and reliably.

Moreover, the processing device is preferably designed to determine the force exerted on the actuator part or at least a measure thereof on the basis of the normalized total force. Accordingly, the exerted force or the measure thereof can also be determined without knowledge of the mass of the actuator part or of the load connected thereto. This also makes it possible, for example, for actuators, in particular lifting columns, to be retro-fitted with the sensor system.

In a further preferred embodiment, the processing device is designed to control the drive on the basis of a quotient from a force exerted on the actuator part, in particular by a user, preferably for moving the actuator part, and from a total force acting when the actuator part is at rest. The processing device can in particular be designed to determine this quotient on the basis of the normalized total force, the total force detected by the force sensor during the movement of the actuator part. The quotient can form a measure of the force exerted on the actuator part for example by a user, in particular by a hand movement of the user, for moving the actuator part. The drive can thus have the actuator part quickly and precisely track the hand movement of the user.

In a further preferred embodiment, the force sensor is designed as a weighing cell. A weighing cell of this kind can be made particularly compact and can therefore be easily integrated in the actuator, in particular at different locations.

In a further preferred embodiment, the force sensor is designed to detect the total force by detection of a cable tension of a cable by which the actuator part is carried. For this purpose, the force sensor can be connected on one side to the cable and on an opposite side to the actuator part. A change of the cable tension from a rest state, for example from the calibration mode, reliably permits the determination of a measure of a force exerted on the actuator part by a user.

In other words, the processing device can be designed to monitor a deviation of the cable tension from a calibration value and in particular to control the drive on the basis of the deviation of the cable tension from the calibration value together with the detected acceleration. The detection of the cable tension can be realized by a particularly simple technique and in a compact manner.

In a further preferred embodiment, the force sensor is designed to detect the total force by detection of a weight which loads a spindle carrying the actuator part. It is e thereby possible for the force sensor to be arranged in a particularly protected manner inside the actuator, for example inside a column element of a lifting column.

An actuator, in particular a lifting column, according to a second aspect of the invention has an actuator base, an actuator part mounted movably relative to the actuator base, a drive for moving the actuator part, and a sensor system according to the first aspect of the invention. The actuator part is preferably designed as a carriage which is movable, for example, along a side face of the actuator base. Moreover, the actuator part is preferably designed to carry a load, for example an X-ray head. The actuator part can for this purpose have a fastening means, for example threaded bores for screwing the load, a locking mechanism for suspending the load, and/or similar.

In a preferred embodiment, the acceleration sensor and the processing device are arranged on and/or in the actuator part. The actuator, in particular the actuator base, can thus be made particularly compact. Alternatively or additionally, the force sensor is also arranged on and/or in the actuator part. This permits direct and therefore less error-prone detection of the total force acting on the actuator part.

In a further preferred embodiment, the force sensor is arranged in a recess of the actuator part. The force sensor can in particular be received in a pocket formed from the actuator part and a side face of the actuator base. The force sensor can thus be protected particularly reliably against external influences that could adversely affect the detection of the total force.

A mobile X-ray system according to a third aspect of the invention has a movable substructure, an actuator according to the second aspect of the invention mounted on the movable substructure, and an X-ray head which is mounted on the actuator part mounted movably relative to the actuator base.

In a method according to a fourth aspect of the invention for moving an actuator part of an actuator, in particular of a lifting column, which is mounted movably relative to an actuator base, (i) a total force acting on the actuator part is detected, and (ii) an acceleration of the actuator part (3) is detected. According to the invention, (iii) a drive of the actuator for moving the actuator part is controlled on the basis of the detected total force and of the detected acceleration, in particular on the basis of a measure for a force exerted on the actuator part. The measure of the force exerted on the actuator part can be determined on the basis of the detected total force and the detected acceleration.

The above description of preferred embodiments of the invention contains numerous features which are represented in part in a manner combined as a plurality of features in the individual dependent claims. However, these features can also be considered individually and combined to form expedient further combinations. In particular, these features are each combinable individually and in any suitable combination with the sensor system according to the first aspect of the invention, with the actuator according to the second aspect of the invention, with the X-ray system according to the third aspect of the invention, and with the method according to the fourth aspect of the invention.

The above-described properties, features and advantages of the invention and the way in which they are achieved are explained in detail, in association with the figures, in the following description of exemplary embodiments of the invention. The same reference signs for the same or corresponding features of the invention are used consistently in the figures. The exemplary embodiments serve to explain the invention and do not limit the invention to the combinations of features specified therein, nor do they limit it with regard to functional features. Moreover, features of each exemplary embodiment which are suitable for this can also be considered explicitly in isolation and be combined with any of the claims.

DESCRIPTION OF THE INVENTION

Figures 1A, 1B:
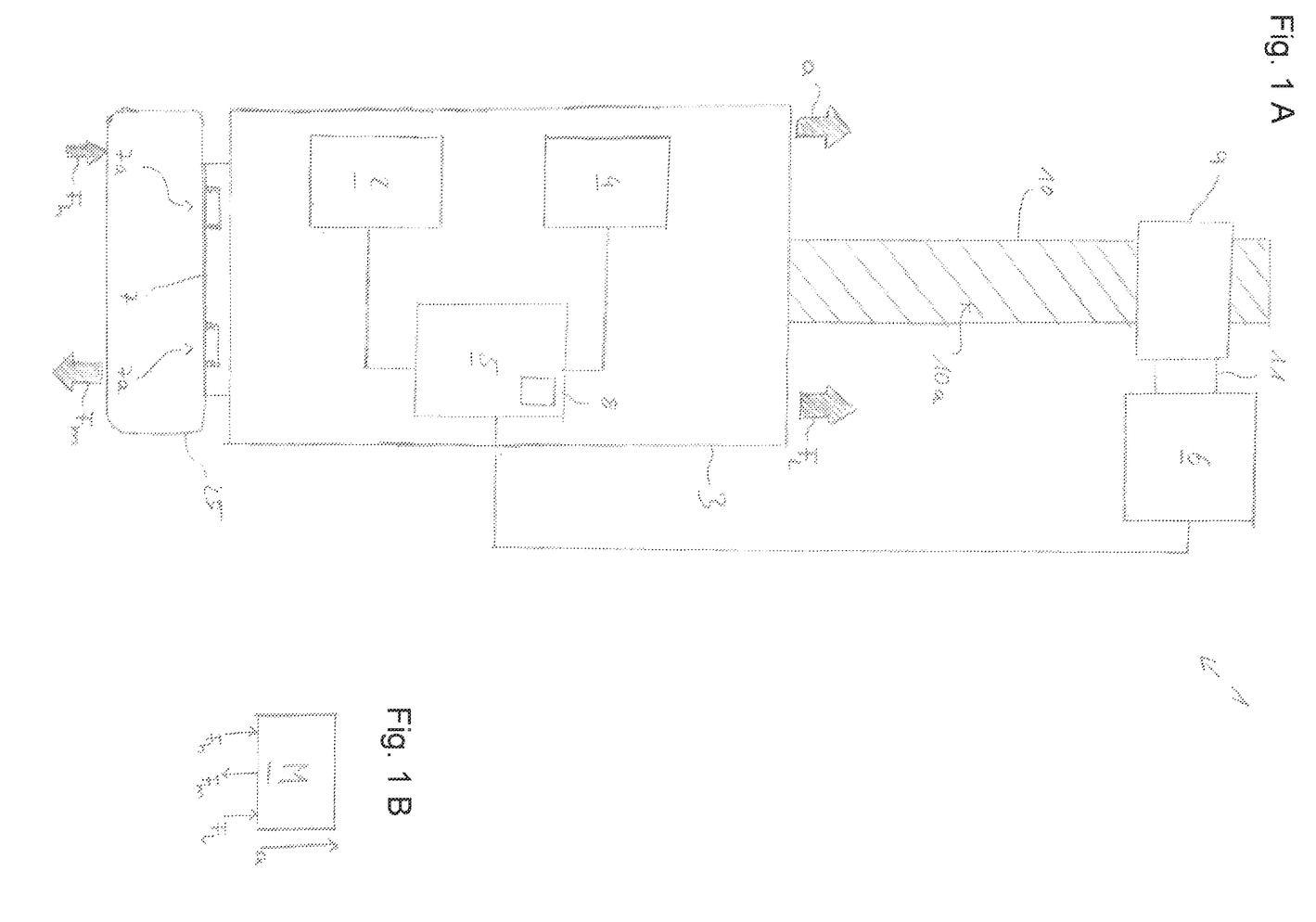
FIG. 1A shows an example of a sensor system for an actuator.
FIG. 1B shows a free-body diagram with the forces acting on a load.

FIG. 1A shows an example of a sensor system 1 for an actuator, in particular a lifting column. The sensor system 1 has a force sensor 2 which is designed to measure a total force $F_I$ acting on an actuator part 3 of the actuator mounted movably relative to an actuator base of the actuator, e.g. a housing (not shown). The sensor system 1 additionally has an acceleration sensor 4 which is designed to detect an acceleration a acting on the actuator part 3. A processing device 5 of the sensor system 1 is designed to control, on the basis of the detected total force $F_I$ and of the detected acceleration a, a drive 6 of the actuator for moving the actuator part 3.

In the example shown, the drive 6 is designed to move a nut 9 in rotation via a gear 11. The nut 9 preferably has an inner thread which is in engagement with an outer thread 10a of a spindle 10. With the aid of the nut 9 and the spindle 10, a rotation movement of a shaft of the drive 6 can therefore be converted into a translation movement of the actuator part 3.

As is indicated in FIG. 1, the force sensor 2, the acceleration sensor 4 and the drive 6 are connected to the processing device 5 in terms of signals and data. At least some of the connections, in particular between the processing device 5 and the drive 6, can also be wireless connections, for example so as not to impede the movement of the actuator part 3 relative to the drive 6.

For moving a load 25 which is connected to the actuator part 3 for example via a fastening means 7, for example by being screwed in threaded bores 7a of the fastening means 7, the user can exert a force $F_h$ on the load 25 and thus also on the actuator part 3. This force $F_h$, exerted for example by the hand of the user, can be detected by the force sensor 2 as part of the total force $F_I$.

FIG. 1B shows a free-body diagram with the forces that act on a load with the mass M. The total force $F_I$ also includes a non-constant (inertial) force $F_I = M \cdot a$, which corresponds to the acceleration a caused by the force exerted on the load 25 or the actuator part 3. As is shown in FIG. 1A and FIG. 1B, this force counters the force $F_h$ exerted on the load 25. The following thus holds for the total force $F_I$:

$$F_I = M \cdot a - F_h.$$

It is therefore only by measuring the acceleration a with the aid of the acceleration sensor 4 that it is possible to determine, with the processing device 5, the force $F_h$ exerted by the user on the load 25 or the actuator part 3 or at least a measure of said force. It is preferably immaterial here whether the load 25 is already in motion, e.g. because the actuator as a whole is moved, for example if the actuator is mounted on a movable platform such as a trolley or vehicle.

The measure of the force $F_h$ can be used as a basis for controlling the drive 6. It is in this way possible for the movement of the load 25, caused by a user, to be assisted by the drive 6.

To permit the assistance by the drive 6 independently of the mass M of the load 25 that is to be moved, the processing device 5, when controlling the drive 6, preferably takes into account a calibration value which is stored, for example, in a memory 8 of the sensor system 1, in particular of the processing device 5.

The calibration value preferably corresponds to a total force $F_{10}$ which is detected by the force sensor 2 in a calibration mode of the sensor system 1 and in which the actuator part 3 is at rest, i.e. is stationary. Since no force $F_h$ is therefore exerted on the load 25 or the actuator part 3 in the calibration mode, and there is no acceleration of the actuator part 3, the total force $F_{10} = M \cdot a_0$ detected by the force sensor 2 corresponds to the weight force, where $a_0$ is the gravitational acceleration.

The processing device 5 is preferably designed to normalize the force $F_t$ measured by the force sensor 2 with the total force $F_{10}$ detected when the actuator part 3 is at rest, such that, as a measure of the force $F_h$ exerted upon movement of the actuator part 3, there is a quotient:

$$\frac{F_h}{F_{10}} = \frac{M \cdot a}{F_{10}} - \frac{F_1}{F_{10}}$$

or $$\frac{F_h}{F_{10}} = \frac{a}{a_0} - \frac{F_1}{F_{10}}.$$

On measuring the acceleration a and the total force $F_t$ acting on the actuator part 3, the quotient $F_h/F_{10}$ can be quickly calculated, i.e. substantially in real time, using the calibration value $F_{10}$ stored in the memory 8 and the gravitational acceleration $a_0$, and it can therefore be used as a basis for controlling the drive 6 in order to achieve tracking of the actuator part 3 or of the load 25 connected thereto.

Figure 2:
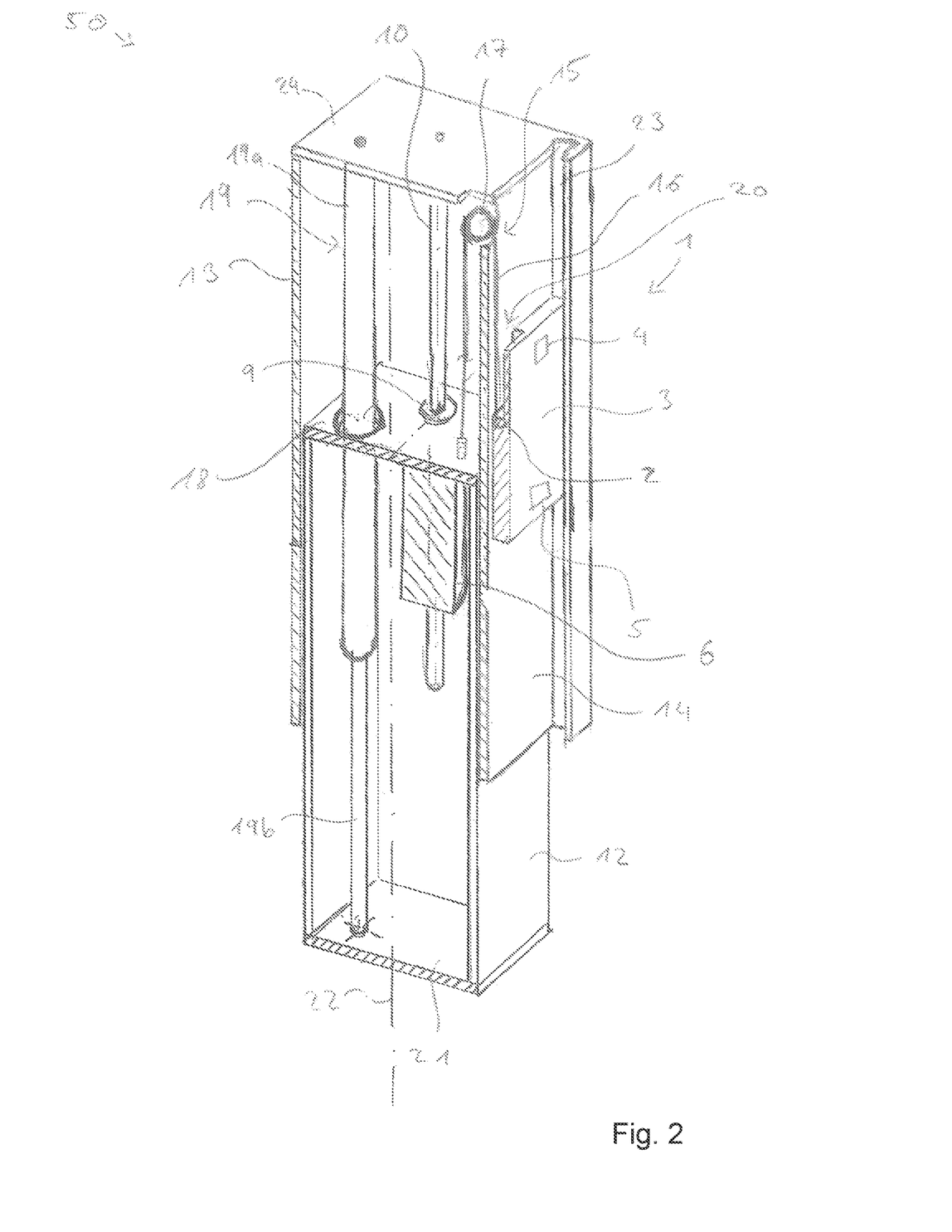
FIG. 2 shows a first example of an actuator with a sensor system in a sectional view.

FIG. 2 shows an example of an actuator 50 with a sensor system 1 in a sectional view. The sensor system 1 has a force sensor 2, an acceleration sensor 4 and a processing device 5. The actuator 50 is designed here as a lifting column which has a first base part 12, a second base part 13, and an actuator part 3. The second base part 13 is designed like a column and is mounted movably, in particular telescopically, relative to the first base part 12, which is likewise designed like a column. The actuator part 3 is mounted movably relative to the second column-like base part 13, in particular movably along a side face 14 of the second base part 13. For this purpose, the actuator part 3 can be designed as a carriage which runs between two guide rails 23, of which only one is visible in FIG. 2. The guide rails 23 run in a longitudinal direction of the actuator 50, i.e. parallel to a longitudinal axis 22.

For moving the components of the actuator 50 relative to each other, a drive 6 in the form of a motor is provided. The drive 6 is arranged on a first closure plate 18 of the e first base part 12, which plate defines an upper end of the first base part 12.

In the example shown, the components of the sensor system 1 are integrated in the actuator part 3, i.e. on or in the actuator part 3. The force sensor 2 is here designed to detect a total force acting on the actuator part 3, while the acceleration sensor 4 is designed to detect an acceleration of the actuator part 3. On the basis of the detected total force and of the detected acceleration, the processing device 5 can control the drive 6 in such a way that a movement of the actuator part 3 executed by a user relative to the base parts 12, 13 is assisted.

The actuator part 3 can for this purpose be connected to the first base part 12 via a cable pull 15. The actuator part 3 is preferably carried by a cable 16 of the cable pull 15, in which case it can be fastened to an outer end of the cable 16. For fastening the cable 16 in the example shown, the actuator part 3 has a recess 20 in which the cable 16 can partially run. The force sensor 2 is arranged for example at an inner end of the recess 20, in particular connected to the cable 16. In this way, the force sensor 2 can detect the total force acting on the actuator part 3 on the basis of the detection of a cable tension of the cable 16.

The cable 16 is guided via a deflection roller 17, which is mounted on the second base part 13, and fastened at a base part end to the first base part 12, in particular to the first closure plate 18. During a movement of the second base part 13 relative to the first base part 12, the cable pull 15 therefore also causes a movement of the actuator part 3 relative to the second base part 13.

For the movement of the second base part 13 relative to the first base part 12, a drive 6, which is arranged on the first closure plate 18 and which can be fastened to the first base part 12 in particular in the region of the first closure plate 18, is coupled to a nut 9, for example via a gear. An inner thread of the nut 9 is in engagement with an outer thread of a spindle 10, such that a rotation of the nut 9 driven by the drive 6 causes a translation of the spindle 10. The spindle 10 is fastened to an upper end of the second base part 13 facing away from the first base part 12, in particular from the first closure oblate 18, in particular to a second closure plate 24 of the second base part 13, such that, during a translation of the spindle 10, the second base part 13 is also moved relative to the first base part 12. At the same time, a movement of the actuator part 3 relative to the second base part 13 is also effected via the cable pull 15.

To be able to support the actuator 50 in an extended state, a weight-compensating means 19 is preferably provided, which can be designed as a gas spring, for example. A cylinder 19a of the gas spring is connected to the second base part 13, while a piston 19b of the gas spring is connected to the first base part 12. The weight force of a load (not shown) connected to the actuator part 3, which also acts on the second base part 13 via the deflection roller 17, can be taken up in this way. This permits a weight compensation of the second base part 13 and of the actuator part 3 or the load coupled thereto, such that, for example, a smaller drive 6 can be used.

In contrast to the example shown in FIG. 2, the drive 6 can also be arranged on a bottom 21 of the first base part 12, which defines a lower end of the first base part 12. The nut 9 can have a sleeve-like design and can extend in the longitudinal direction of the actuator 50, i.e. parallel to the longitudinal axis 22, substantially through the entire first base part 12, in order to be able to interact with the spindle 10 even when the second base part 13 is fully extended. Of course, it is also possible to change around the arrangement of nut 9 and spindle 10, such that the spindle 10 is moved in rotation by the drive 6 and causes a translation of the nut 9. The described effects do not change as a result.

Likewise in contrast to the example shown in FIG. 2, instead of the inner end of the cable 16 being fastened to the first closure plate 18, a further drive can also be provided with which the actuator part 3 can be moved relative to the first base part 12, if appropriate independently of the movement of the second base part 13.

The further drive (not shown in FIG. 2) can be designed, for example, to drive a cable drum on which the cable 16 can be wound and unwound. By corresponding control of the further drive, it is thus possible to shorten or lengthen the cable 16 and thus move the actuator part 3 along the side face 14.

Figure 3:
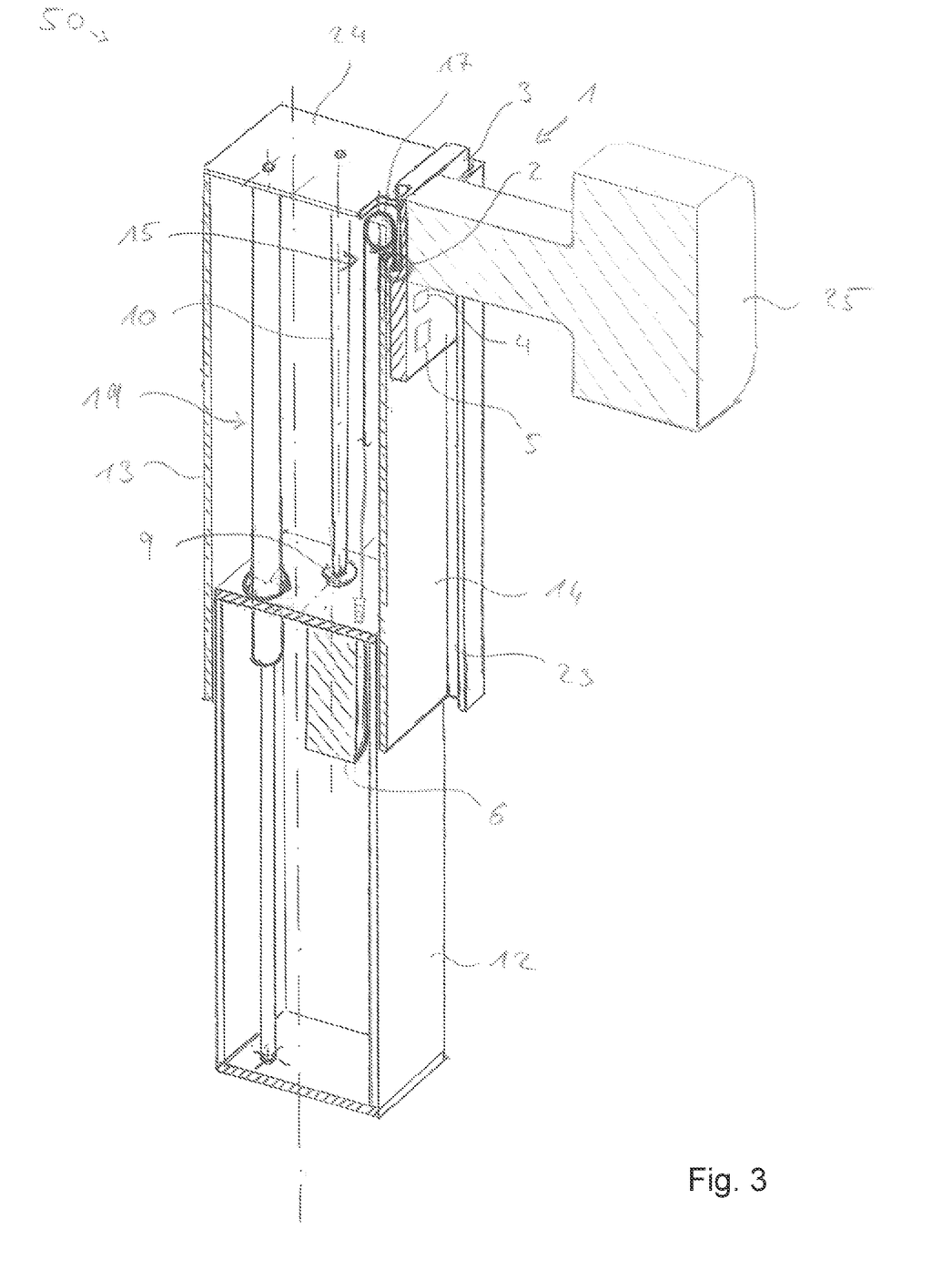
FIG. 3 shows a second example of an actuator with a sensor system in a sectional view.

FIG. 3 shows a second example of an actuator 50 with a sensor system 1 in a sectional view, in which the load 25 carried by an actuator part 3 is also shown schematically. Both the actuator 50 and the sensor system 1 largely correspond to the actuator and sensor system shown in FIG. 2. In particular, the sensor system 1 likewise has a force sensor 2 for detecting a total force acting on an actuator part 3, and an acceleration sensor 4 for detecting an acceleration of the actuator part 3. A processing device 5 is designed to control a drive 6, with which the carriage-like actuator part 3 guided by guide rails 23 is movable along a side face 14 of a second base part 13, on the basis of the detected total force and of the detected acceleration. The second base part 13 here is likewise mounted movably, in particular telescopically, relative to a first base part 12.

As in the example shown in FIG. 2, the force sensor 2 is arranged on or in the actuator part 3. In principle, however, it is also possible to arrange the force sensor 2 at another location, as long as the force sensor 2 can there detect all of the total force acting on the actuator part 3. For example, the force sensor 2 can be arranged on an upper end of the second base part 13 opposite the first base part, in particular on a second closure plate 24 of the second base part 13, which plate defines an upper end of the second base part 13, if no weight-compensating means 19 provided, i.e. no part of the total force is compensated. The force sensor 2 could preferably be connected on one side to the second base part 13 and on an opposite side to a spindle 10 which converts a rotation of a nut 9, driven by the drive 6, into a translation and thereby causes the movement of the second base part 13 relative to the first base part 12.

In this exemplary embodiment (not shown in FIG. 3) without weight-compensating means 19, the force sensor 2 thus lies protected in the interior of the second base part 13 and can detect the total force acting on the actuator part 3 by the detection of a weight placed on the spindle 10 by the load 25. The load 25, for example an X-ray head, is fastened to the actuator part 3. By way of the deflection roller 17 of a cable pull 15, the weight of the load 25 transfers to the second base part 13, where it could then be detected.

Figure 4:
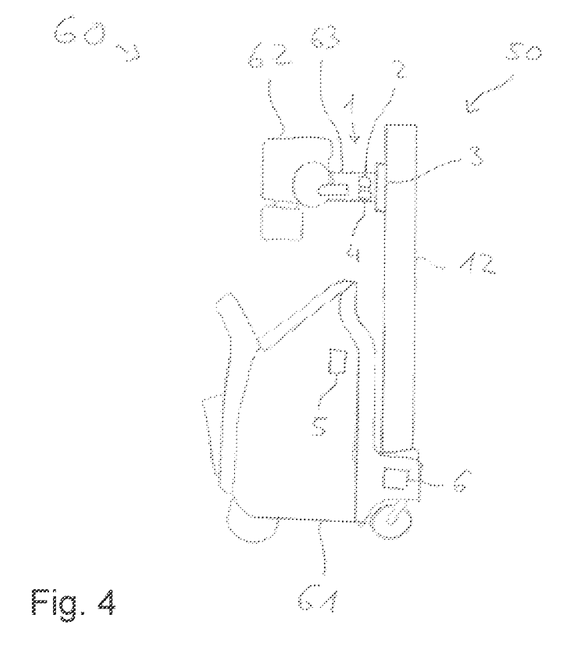
FIG. 4 shows an example of a mobile X-ray system.

FIG. 4 shows an example of a mobile X-ray system 60 with an actuator 50 which is designed as a lifting column 50 and which has a base part 12, an actuator part 3 mounted movably relative to the base part 12, a drive 6 for moving the actuator part 3, and a sensor system 1 with a force sensor 2, an acceleration sensor 4 and a processing device 5. The X-ray system 60 has a movable substructure 61 which, in the present example, is designed as a three-wheeled or four-wheeled trolley. The X-ray system 60 additionally has an X-ray head 62 for generating X-ray radiation. The X-ray head 62 is mounted on the actuator part 3 preferably with the aid of a linear actuator 63 and can thus be positioned relative to a patient, for example.

The force sensor 2 is designed to detect a total force acting on the X-ray head 62 connected to the actuator part 3, for example when the X-ray head 62 is guided by hand by a user for positioning. The acceleration sensor 4 is designed to detect the acceleration of the X-ray head 62, for example in such a movement. The processing device 5 is designed to control the drive 6 for moving the actuator part 3 and thus also the X-ray head 62 relative to the base part 12, specifically on the basis of the detected total force and of the detected acceleration. A movement of the X-ray head 62 guided by the user can thus be assisted by the drive 6. This significantly reduces the force that the user has to apply for the movement and permits intuitive and rapid positioning of the X-ray head 62 despite the heavy weight of the latter.

Figure 5:
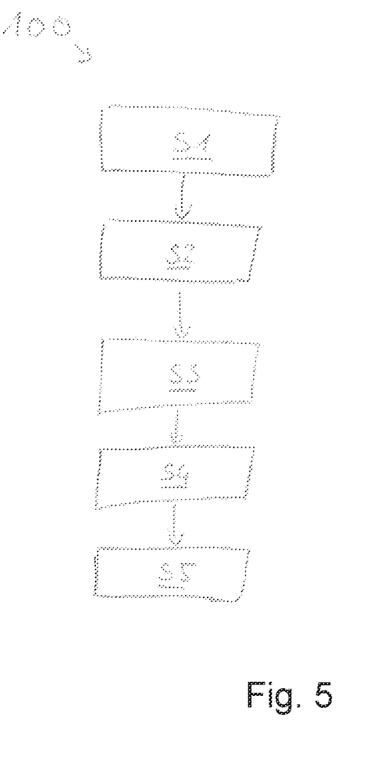
FIG. 5 shows an example of a method for moving an actuator part.

FIG. 5 shows an example of a method 100 for moving an actuator part of an actuator relative to a base part of the actuator.

In a method step S1, the sensor system is operated in a calibration mode. A total force acting on the actuator part is detected with the actuator part at rest, i.e. while the actuator part is not in motion or is in a stationary state. For this purpose, a force sensor is preferably provided which, for example, can be arranged in such a way that it supports or carries the actuator part, possibly also indirectly. In the calibration mode, with the actuator part not in motion, the force sensor thus largely detects the weight force of the actuator part or of a load fastened to the latter.

In the context of method step S1, the total force detected by the force sensor, with the actuator part at rest, is preferably stored as a calibration value in a memory. The calibration mode can then be ended.

In a further method step S2, the total force acting on the actuator part is detected when the sensor system is no longer in the calibration mode. i.e. for example when the actuator part is moved by a user. The total force can then be composed of a plurality of forces, for example the weight force of the actuator, the (inertial) force caused by an acceleration, and a force exerted on the actuator part by the user for the movement. In relation to the calibration mode, the total force detected by the force sensor upon movement of the actuator part changes accordingly.

In a further method step S3, an acceleration of the actuator part is detected which, for example, is caused by the movement of the actuator part by the user. For this purpose, an acceleration sensor can be provided.

In a further method step S4, a measure of the force exerted on the actuator part, for example by the user, is determined, specifically on the basis of the detected total force and the detected acceleration. The detected total force can be normalized with the stored calibration value. Preferably, the detected acceleration is also normalized with a normalization value, in particular the gravitational acceleration. The normalization value can be stored in the memory too, i.e. together with the calibration value.

A quotient from the force exerted on the actuator part and from the calibration value is preferably determined as a measure of the force exerted on the actuator part.

In a further method step S5, a drive, which is designed to move the actuator part relative to the base part, is controlled on the basis of the determined measure of the force exerted on the actuator part. In this way, the actuator part can reliably and precisely track a movement executed by the user.

LIST OF REFERENCE SIGNS 1 sensor system
2 force sensor
3 actuator part
4 acceleration sensor
5 processing device
6 drive
7 fastening means
7a threaded bore
8 memory
9 nut
10 spindle
10a outer thread
11 gear
12 first base part
13 second base part
14 side face
15 cable pull
16 cable
17 deflection roller
18 first closure plate
19 weight-compensating means
19a cylinder
19b piston
20 recess
21 bottom
22 longitudinal axis 23 guide rail
24 second closure plate
25 load
50 actuator
60 X-ray system
61 substructure
62 X-ray head
63 linear actuator
100 method
S1-S5 method steps
$F_t$ total force
a acceleration
$F_h$ exerted force
M mass

The invention claimed is:

1. A sensor system for an actuator, the sensor system comprising:
   a force sensor configured to detect a total force acting on an actuator part mounted movably relative to an actuator base;
   an acceleration sensor configured to detect an acceleration of the actuator part; and
   a processor configured to control a drive of the actuator for moving the actuator part on a basis of the total force detected and the acceleration detected, said processor further configured to use the total force and the acceleration to determine a measure of a force exerted on the actuator part by a user for moving the actuator part and to control the drive on a basis of the measure of the force.

2. The sensor system according to claim 1, wherein said processor is configured to further control the drive on a basis of a stored calibration value.

3. The sensor system according to claim 2, wherein the stored calibration value corresponds to a total force acting on the actuator part when the actuator part is at rest.

4. The sensor system according to claim 3, wherein said force sensor is configured to detect the total force acting on the actuator part, when the actuator part is at rest, in a calibration mode.

5. The sensor system according to claim 1, wherein said processor is configured to normalize the total force, detected by said force sensor, with a total force acting on the actuator part when the actuator part is at rest.

6. The sensor system according to claim 1, wherein said processor is configured to further control the drive on a basis of a quotient from a force exerted on the actuator part by a user for movement and a total force acting when the actuator part is at rest.

7. The sensor system according to claim 1, wherein said force sensor is a weighing cell.

8. The sensor system according to claim 1, wherein said force sensor is configured to detect the total force by detection of cable tension of a cable by which the actuator part is carried.

9. The sensor system according to claim 1, wherein said force sensor is configured to detect the total force by detection of a weight which loads a spindle carrying the actuator part.

10. An actuator, comprising:
    an actuator base;
    an actuator part mounted movably relative to said actuator base;
    a drive for moving said actuator part; and
    a sensor system, containing:
      a force sensor configured to detect a total force acting on said actuator part;
      an acceleration sensor configured to detect an acceleration of said actuator part; and
      a processor configured to control said drive for moving said actuator part on a basis of the total force detected and the acceleration detected, said processor configured to use the total force and the acceleration to determine a measure of a force exerted on said actuator part by a user for moving said actuator part and to control said drive on a basis of the measure of the force.

11. The actuator according to claim 10, wherein said acceleration sensor and said processor are disposed on and/or in said actuator part.

12. The actuator according to claim 10, wherein said actuator part has a recess formed therein, said force sensor is disposed in said recess of said actuator part.

13. The actuator according to claim 10, wherein the actuator is a lifting column.

14. A mobile X-ray system, comprising:
    a movable substructure;
    an actuator according to claim 10 mounted on said movable substructure; and
    an X-ray head mounted on said actuator part mounted movably relative to said actuator base.

15. A method for moving an actuator part of an actuator being mounted movably relative to an actuator base, which comprises the steps of:
    detecting a total force acting on the actuator part;
    detecting an acceleration of the actuator part; and
    controlling, via a processor, a drive of the actuator for moving the actuator part on a basis of the total force detected and the acceleration detected, wherein the processor is configured to use the total force and the acceleration to determine a measure of a force exerted on the actuator part by a user for moving the actuator part and to control the drive on a basis of the measure of the force.

* * * * *